(12) United States Patent
Lynn et al.

(10) Patent No.: US 7,112,361 B2
(45) Date of Patent: Sep. 26, 2006

(54) METHODS OF MAKING DECOMPOSABLE THIN FILMS OF POLYELECTROLYTES AND USES THEREOF

(75) Inventors: David M. Lynn, Middleton, WI (US); Eduardo Vazquez, Bayamon, PR (US); Robert Langer, Newton, MA (US); Paula T. Hammond, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 84 days.

(21) Appl. No.: 10/280,268

(22) Filed: Oct. 24, 2002

(65) Prior Publication Data

US 2003/0124368 A1 Jul. 3, 2003

Related U.S. Application Data

(60) Provisional application No. 60/335,213, filed on Oct. 25, 2001.

(51) Int. Cl.
*B32B 7/02* (2006.01)

(52) U.S. Cl. .................. 428/212; 428/402; 428/402.2; 428/402.21; 428/402.22; 428/402.24; 428/403; 428/480; 428/483; 428/702; 428/426; 428/446; 428/454; 428/457

(58) Field of Classification Search ............... 428/212, 428/402, 402.2, 402.21, 402.24, 403, 404, 428/405, 406, 407, 430, 458, 483
See application file for complete search history.

(56) References Cited

U.S. PATENT DOCUMENTS

| | | | | |
|---|---|---|---|---|
| 4,191,811 A | | 3/1980 | Hodgdon | 521/27 |
| 4,250,029 A | * | 2/1981 | Kiser et al. | 210/652 |
| 5,208,111 A | * | 5/1993 | Decher et al. | 428/420 |
| 5,364,634 A | | 11/1994 | Lew | 424/451 |
| 5,462,990 A | | 10/1995 | Hubbell et al. | 525/54.1 |
| 5,518,767 A | * | 5/1996 | Rubner et al. | 427/259 |
| 5,536,573 A | * | 7/1996 | Rubner et al. | 428/378 |
| 5,630,941 A | * | 5/1997 | Burger et al. | 210/490 |
| 5,700,559 A | * | 12/1997 | Sheu et al. | 428/319.7 |
| 5,716,709 A | * | 2/1998 | Ferguson et al. | 428/420 |
| 5,807,636 A | * | 9/1998 | Sheu et al. | 428/403 |
| 5,837,377 A | * | 11/1998 | Sheu et al. | 428/412 |
| 5,858,746 A | | 1/1999 | Hubbell et al. | 435/177 |
| 5,904,927 A | | 5/1999 | Amiji | 424/422 |
| 5,962,520 A | | 10/1999 | Smith et al. | 514/529 |
| 6,022,590 A | * | 2/2000 | Ferguson et al. | 427/354 |
| 6,060,582 A | | 5/2000 | Hubbell et al. | 528/354 |
| 6,114,099 A | * | 9/2000 | Liu et al. | 430/324 |
| 6,402,918 B1 | * | 6/2002 | Schlenoff et al. | 204/601 |
| 6,447,887 B1 | * | 9/2002 | Claus et al. | 428/209 |
| 6,451,871 B1 | * | 9/2002 | Winterton et al. | 523/106 |

(Continued)

FOREIGN PATENT DOCUMENTS

DE 19812083 9/1999

(Continued)

OTHER PUBLICATIONS

Anderson, "Human Gene Therapy" *Nature*, 392: 25-30, 1996.

(Continued)

*Primary Examiner*—Vivian Chen
(74) *Attorney, Agent, or Firm*—Choate, Hall & Stewart LLP; Valarie B. Rosen

(57) ABSTRACT

A decomposable thin film comprising a plurality of polyelectrolyte layers of alternating charge, wherein decomposition of the thin film is characterized by degradation of at least a portion of the polyelectrolyte layers.

27 Claims, 10 Drawing Sheets

U.S. PATENT DOCUMENTS

| | | | | |
|---|---|---|---|---|
| 6,479,146 | B1 * | 11/2002 | Caruso et al. | 428/403 |
| 6,492,096 | B1 * | 12/2002 | Liu et al. | 430/324 |
| 6,699,501 | B1 * | 3/2004 | Neo et al. | 424/463 |
| 6,743,521 | B1 * | 6/2004 | Hubbell et al. | 428/500 |
| 2002/0053514 | A1 * | 5/2002 | Locascio et al. | 204/454 |
| 2002/0131951 | A1 * | 9/2002 | Langer et al. | 424/78.37 |
| 2002/0187197 | A1 * | 12/2002 | Caruso et al. | 424/490 |
| 2004/0044100 | A1 * | 3/2004 | Schlenoff et al. | 523/206 |
| 2004/0149572 | A1 * | 8/2004 | Schlenoff et al. | 204/296 |

FOREIGN PATENT DOCUMENTS

| | | |
|---|---|---|
| EP | 1 116 516 A1 * | 7/2001 |
| GB | 1213803 | 11/1970 |
| GB | 1213805 | 11/1970 |
| WO | WO 96/03147 | 2/1996 |
| WO | WO 98/47948 * | 10/1998 |
| WO | WO 99/47253 | 9/1999 |
| WO | WO 00/77281 | 12/2000 |
| WO | WO 00/77281 A1 * | 12/2000 |
| WO | WO 01/57118 A2 * | 8/2001 |
| WO | WO 01/94441 | 12/2001 |

OTHER PUBLICATIONS

Anderson, et al., "Biodegradation and Biocompatibility of PLA and PLGA Microspheres" *Adv. Drug Delivery Rev.* 28:5-24,1997.

Ando, et al., "PLGA Micospheres Containing Plasmid DNA: Preservation of Supercoiled DNA via Cryopreparation and Carbohydrate Stabilization" *J. Pharm. Sci.* 88: 126-130, 1999.

Barrera, et al., "Synthesis and RGD Peptide Modification of a New Biodegradable Copolymer: Poly (lactic acid-co-lysine)" *J. Am. Chem. Soc.* 115:11010-11011, 1993.

Behr, "Synthetic Gene-Transfer Vectors" *Acc. Chem. Res.* 26: 274-278, 1993.

Behr, "The Proton Sponge: a Trick to Enter Cells the Viruses Did Not Expoit" *Chimia*, 51: 34-36, 1997.

Boussif, et al., "A Versatile Vector for Gene and Oligonucleotide Transfer into Cells in Culture and In Vivo: Polyethylenimine" *Proc. Natl. Acad. Sci, USA*, 92: 7297-7301, 1995.

Brazeau, et al., "In Vitro Myotoxicity of Selected Cationic Macromolecules Used in Non-Vital Gene Delivery" *Pharm. Res.* 15: 680-684, 1998.

Choksakulnimitr et al., "In Vitro Cytotoxicity of Macromolecules in Different Cell Culture Systems" *Controlled Release*, 34: 233-241, 1995.

Cotten, et al., "Receptor-Mediated Transport of DNA into Eukaryotic Cells" *Methods Enzym.* 217: 618, 1993.

Crystal, "Transfer of Genes to Humans: Early Lessons and Obstacles to Success"*Science*, 270: 404-410, 1995.

Danusso, et al., "Synthesis of Tertiary Amine Polymers" *Polymer*, 11:88-113, 1970.

Demeneix, et al., In *Artificial Self-Assembling Systems for Gene Delivery* (Felgner, et al., Eds). American Chemical Society, Washington, D.C., 1996, 146-151.

Deshmukh, et al., "Liposome and Polylysine Mediated Gene Transfer" *New J. Chem.* 21: 113-124, 1997.

Ferruti, et al., "Linear Amino Polymers: Synthesis, Protonation and Complex Formation" *Advances in Polymer Science*, 58: 55-92, 1984.

Ferruti, et al., "Recent Results on Functional Polymers and Macromonomers of Interest as Biomaterials or for Biomaterial Modifcation" *Biomaterials*, 15: 1235-1241, 1994.

Ferruti, et al., "Synthesis, Characterisation and Antitumour Activity of Platinum (II) Complexes of Novel Functionalised Poly (Amido Amine)s" *Macromol. Chem. Phys.* 200: 1644-1654, 1999.

Ferruti, et al., "Synthesis, Physico-Chemical Properties and Biomedical Applications of Poly(amino-amine)s" *Polymer*, 26: 1336, 1985.

Fire, et al., "Potent and Specific Genetic Interference by Double-Stranded RNA in Caenorhabditis Elegans" *Nature*, 391: 806-811, 1998.

Friedman, "Human Gene Therapy—An Immature Genie,k but Certainly out of the Bottle" *Nature Med,* 2: 144-147, 1996.

Gerasimov, et al., "Cytosolic Drug Delivery Using pH- and Light Sensitive Liposomes" *Adv. Drug Delivery Rev.* 38: 317-338, 1999.

Gonzalez, et al., "New Class of Polymers for the Delivery of Macromolecular Therapeutics" *Bioconjugate Chem.* 10: 1068-1074, 1999.

Haensler, et al., "Polyamidoamine Cascade Polymers Mediate Efficient Transfection of Cells In Culture" *Bioconjugate Chem.* 4: 372-379, 1993.

Hanes, et al., "New Advances in Microsphere-Based Single-Dose Vaccines" *Adv. Drug Delivery Rev.* 28: 97-119, 1997.

Hansen, et al., "Re-Examination and Further Development of a Precise and Rapid Dye Method for Measuring Cell Growth/Cell Kill" *Immunol. Methods,* 119:203-210, 1989.

Hill, et al., "In Vitro Cytotoxicity of Poly(amidoamine)s: Relevance to DNA Delivery" *Biochim. Biophys. Acta,* 1427: 161-174, 1999.

Hope, et al., Cationic Lipids, Phosphatidylethanolamine and the Intracellular Delivery of Polymeric, Nucleic Acid-Based Drugs (Review), *Molecular Membrane Technology*, 15: 1-14, 1998.

Kabanov, et al., "DNA Complexes with Polycations for the Delivery of Genetic Material inot Cells" Bioconjugate Chem. 6:7-20, 1995.

Kargina, et al., "Self-Splitted Water-Soluble Ionogenic Polymers" *Vysokomol. Soedin. Seriya A,* 28: 1139-1144, 1986.

Kukowska-Latallo, et al., "Efficient Transfer of Genetic Material into Mammalian Cells Using Starburst Polyamidoamine Dendrimers" *Proc. Natl. Acad. Sci. USA,* 93: 4897-4902, 1996.

Kwon, et al., "Pseudopoly (Amino Acids): A Study of the Synthesis and Characterization of Poly(trans-4-hydroxy-N-acyl-L-proline esters)" *Macromolecules,* 22: 3250-3255, 1989.

Lim, et al., "A Self-Destroying Polycationic Polymer: Biodegradable Poly(4-Hydroxy-L-Proline Ester)" *J. Am. Chem. Soc.* 121: 5633-5639, 1999.

Lim, et al., "Development of a Safe Gene Delivery System Using Biodegradable Polymer, Poly [α-(4-Aminobutyl-L-Glycolic Acid]" *J. Am. Chem. Soc.* 122: 6524-6525, 2000.

Linhardt, et al., "Free-Radical Synthesis of Poly(2-Ethylacrylic Acid) Fractions of Low Polydispersity: Effects of Molecular Weight and Polydispersity on the pH-Dependent Conformational Transition in Aqueous Solution" *Macromolecules,* 32: 4457-4459, 1999.

Linhardt, et al., "pH-Induced Fusion and Lysis of Phosphatidylcholine Vesicles by Hydrophobic Polyelectrolyte Poly(2-ethylacrylic Acid)" *Langmuir,* 16: 122-127, 2000.

Luo, et al., "Synthetic DNA Delivery Systems" *Nat. Biotechnol.* 18: 33-37, 2000.

Mathiowitz, et al., "Polyanhydride Microspheres as Drug Carriers I. Hot-Melt Microencapsulation" *J. Controlled Release,* 5:13-22, 1987.

Mathiowitz, et al., "Polyanhydride Microspheres as Drug Carriers. II. Microencapsulation" *J. Appl. Polymer Sci.,* 35: 755-774, 1988.

Miller, "Cationic Liposomes for Gene Therapy" *Angew. Chem. Int. Ed.* 37: 1769-1785, 1998.

Mulligan, "The Basic Science of Gene Therapy" *Science,* 260: 926-932, 1993.

Murphy, et al., "A Combinatorial Approach to the Delivery of Efficient Cationic Peptoid Reagents for Gene Delivery", *Proc. Natl. Acad. Sci. USA,* 95: 1517-1522, 1998.

O'Donnell, et al., "Preparation of Microspheres by the Solvent Evaporation Technique" *Adv. Drug Delivery Rev.,* 28:25-42, 1997.

Okada, "One-and Three-Month Release Injectable Microspheres of the LH-RH Superagonist Leuprorelin Acetate" *Adv. Drug Delivery Rev.* 28: 43-70, 1997.

Putnam, et al., "Poly(4-hydroxy-L-proline ester): Low-Temperature Polycondensation and Plasmid" *Macromolecules* 32: 3658-3662, 1999.

Rao, et al., "Poly (Butaneodiol Spermate): A Hydrolytically Labile Polyester-Based Nitric Oxide Carrier" *J. Bioactive and Compatible Polymers* 14: 54-63, 1999.

Roberts, et al., "Preliminary Biological Evaluation of Polyamidoamine (PAMAM) Starburst™ Dendrimers" *J. Biomed. Mater. Res.* 30: 53-65, 1996.

Sanford, "The Biolistic Process" Trends Biotechnol. 6: 288-302, 1988.

Schaffer, et al., "Vector Unpacking as a Potential Barrier for Receptor-Mediated Polyplex Gene Delivery" *Biotechnolo. Bioeng.* 67: 598-606, 2000.

Schweikl, et al., "Triethylene Glycol Dimethacrylate Induces Large Deletions in the Hprt Gene of V79 Cells" *Mutat. Res.* 438: P71:P78, 1999.

Singh, et al., "Cationic Microparticles: A Potent Delivery System for DNA Vaccines" *Proc. Natl. Acad. Sci. USA*, 97: 811-816, 2000.

Tang, et al., "In Vitro Gene Delivery by Degraded Polyamidoamine Dendrimers" *Bioconjugate Chem.* 7:703-714, 1996.

Uhrich, "Hyperbranched Polymers for Drug Delivery" *Trends Polym. Sci.* 5: 388-393, 1997.

van de Wetering, et al., "Structure-Activity Relationships of Water-Soluble Cationic Methacrylate/Methacrylamide Polymers for Nonviral Gene Delivery" *Bioconjugate Chem.* 10: 589-597, 1999.

Yang, et al., "A New Approach to Identifying Genotoxic Carcinogens: p53 Induction as an Indicator of Genotoxic Damage" *Carcinogenesis*, 19: P1117- P1125, 1998.

Zauner, et al., "Polylysine-Based Transfection Systems Utilizing Receptor-Mediated Delivery" *Adv. Drug. Del. Rev.* 30: 97-113, 1998.

Zhou, et al., "Preparation of Poly(L-serine ester): A Structural Analogue of Conventional Poly(L-serine)" *Macromolecules*, 23: 3399-3406, 1990.

Bass, Brenda L., "RNA Interference The Short Answer", *Nature* 411, 428-429, 2001.

Ferruti, et al., "Amphoteric Linear Poly(amido-amine)s as Endosomolytic Polymers: Correlation between Physicochemical and Biological Properties", *Macromolecules*, 2000.

Kargina O.V., "Self-Spltted Water-Soluble Iogenic Polymers", Water-Soluble Generating vol. 6, pp. 1139-1144, 1986.

Dubas, et al., "Multiple Membranes from 'True' Polyelectrolyte Multilayers", *J. Am. Chem. Soc.*, 123, 5368-5369 (2001).

\* cited by examiner

SPS     PAA     LPEI     PDAC

PAZO

TEMPLATE → MULTILAYER DEPOSITION → COATED PARTICLE → TEMPLATE REMOVAL → HOLLOW CAPSULE

POLY 1

METHODS OF MAKING DECOMPOSABLE THIN FILMS OF POLYELECTROLYTES AND USES THEREOF

This application claims the priority of U.S. Provisional Application No. 60/335,213, filed Oct. 25, 2001, the entire contents of which are incorporated herein by reference.

GOVERNMENT FUNDING

The work described herein was supported, in part, by grants from the National Institutes of Health (GM26698; NRSA Fellowship #1 F32 GM20227-01). Accordingly, the Government may have certain rights in this invention.

BACKGROUND OF THE INVENTION

The layer-by-layer (LBL) adsorption of oppositely-charged polyelectrolytes on surfaces has emerged as a simple, versatile, and inexpensive technique for the fabrication of thin multi-layer films, often with nanometer-scale control over the spatial distribution of ionized species within a film (Decher, G., *Science*, 277:1232–1237, 1997; Hammond P. T., *Curr. Opin. Coll. Interface Sci.*, 3:32–39, 1998). First introduced by Decher in the early 90's (see Decher and Hong, *Ber. Bunsenges. Phys. Chem.* 95:1430, 1991 and Decher, *Science*, 277:1232, 1997), the LBL approach is based on electrostatic attractions between polyelectrolytes and oppositely charged surfaces. In the example shown in FIG. 1, a negatively charged substrate is first dipped in a polycation solution. Electrostatic attractions result in deposition of the polycation and a resulting reversal of surface charge (see FIG. 1, step 1). The positively charged substrate is then submerged in a polyanion solution, resulting in deposition of the polyanion and restoration of the negative charge on the surface (see FIG. 1, step 2). Repetition of these steps leads to the buildup of layers of alternating oppositely charged polyelectrolytes on the substrate surface. In addition to electrostatics, other factors and secondary interactions such as hydrophobicity, salt interactions, solvent quality, polymer concentrations, and deposition time may affect the multi-layer growth of the film (for a review of these factors, see Dubas and Schlenoff, *Macromolecules* 32:8153, 1999, the contents of which are incorporated herein by reference).

The array of materials available for LBL assembly is broad, including synthetic polyelectrolytes, conducting polymers, dyes, and metal colloids, as well as a variety of biological species such as proteins, viruses, and DNA. Applications as diverse as conductive and light-emitting films, biologically-active surfaces, selective membranes, patterned films, and hollow multi-layer structures underscore the potential of the LBL technique (for a review of applications, see Hammond, *Curr. Opin. Coll. Interface Sci.* 3:32, 1998, the contents of which are incorporated herein by reference).

Despite the incorporation of new functionality, there are relatively few examples of multi-layer thin films designed to release incorporated or encapsulated compounds. In particular, there remains a need in the art for thin film controlled release systems that function under physiological conditions.

SUMMARY OF THE INVENTION

In one aspect, the invention is a decomposable thin film. The thin film comprises a plurality of polyelectrolyte layers of alternating charge. For example the thin film may comprise alternating polycationic and polyanionic layers. In certain embodiments, decomposition of the thin film is characterized by hydrolytic degradation of at least a portion of the polyelectrolyte layers. Additionally or alternatively, decomposition of the thin film may be characterized by enzymatic, thermal, and/or photolytic degradation of at least a portion of the polyelectrolyte layers. The degradation rate need not be constant. The degradable polyelectrolytes may be synthetic, natural, or a mixture of both. The polyelectrolyte layers may, for example, include hydrolytically degradable polymers such as polyesters, polyanhydrides, polyorthoesters, polyphosphazenes, polyphosphoesters, or any combination thereof. An anionic and/or cationic group may be incorporated into the polymer backbone, covalently attached to the polymer backbone, or attached to a pendant group of the polymer. The degradable polyelectrolytes may be zwitterionic polymers. The polyelectrolyte layers may further include biodegradable polyelectrolytes. Additionally, the polyelectrolyte layers may include a mixture of degradable and non-degradable polyelectrolytes. The degradation rate of the polyelectrolyte layers may be varied such that the decomposition rate of the thin film is not a constant. A layer of cells may be deposited on the surface of the thin film. The thin films may include electroactive polymers. A portion of the layers may comprise a biomolecule, small molecule, bioactive agent, or some combination of these. The concentration of the biomolecule, small molecule, or bioactive agent may vary with depth, and it may be associated with or mixed with the polyelectrolytes in a layer of the thin film. A cell adhesion sequence, targeting sequence, or both may be disposed in the top layer of the thin film. The film may be deposited upon a non-planar substrate or may be a hollow shell. The substrate may diffuse through the thin film or dissolve after decomposition of the thin film.

In another aspect, the invention is a method of releasing an entity from a thin film. The method comprises associating or mixing the entity with a thin film comprising a plurality of polyelectrolyte layers of alternating charge and placing the thin film in a medium in which at least a portion of the thin film decomposes via the substantially sequential degradation of at least a portion of the polyelectrolyte layers. The degradation may be at least partially hydrolytic, at least partially enzymatic, at least partially thermal, and/or at least partially photolytic. The substrate material may be allowed to diffuse through the thin film or may be dissolved following decomposition of the thin film. The method may further comprise placing the thin film in a second medium in which a second portion of the thin film decomposes. The medium may be characterized by endosomal conditions or physiological conditions. The method may include adding a primer layer interposed between the thin film and the substrate. The method may further comprise producing the thin film via layer-by-layer assembly. For example, the polyelectrolyte layers may be deposited by dip coating, spray coating, brush coating, roll coating, spin casting, or some combination of these. After predetermined layers are deposited, the entity may be associated with them.

In another aspect, the invention is a method of generating a three dimensional microstructure on a substrate surface. The method comprises creating a charged region on a substrate surface, depositing a plurality of polyelectrolyte layers of alternating charge on the charged region, depositing a first non-degradable material over the substrate and the plurality of polyelectrolyte layers, and placing the coated substrate in a medium in which at least a portion of the polyelectrolyte layers degrade. The surface composition of the substrate may vary. The charged region may be created by stamping a self-assembled monolayer, by depositing a uniform coating of a polymer on the substrate surface and patterning the uniform coating by photolithography, or by selectively exposing the substrate surface to plasmas, electromagnetic radiation, or electron beams. Following a step of depositing the first non-degradable material, the method may further comprise creating a charged region on the first non-degradable material, depositing a plurality of polyelectrolyte layers of alternating charge on the charged region, and depositing a second non-degradable material over the first non-degradable material and the plurality of layers. Of course, the two non-degradable materials may be the same or different and the methods used to create the charged region or regions may be the same or different.

DEFINITIONS

"Animal": The term animal, as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). An animal may be a transgenic animal.

"Associated with": When two entities are "associated with" one another as described herein, they are linked by a direct or indirect covalent or non-covalent interaction. Desirable non-covalent interactions include hydrogen bonding, van der Waals interactions, hydrophobic interactions, magnetic interactions, electrostatic interactions, etc. Preferred non-covalent interactions are electrostatic interactions and hydrogen bonds.

"Biomolecules": The term "biomolecules", as used herein, refers to molecules (e.g., proteins, amino acids, peptides, polynucleotides, nucleotides, carbohydrates, sugars, lipids, nucleoproteins, glycoproteins, lipoproteins, steroids, etc.) whether naturally-occurring or artificially created (e.g., by synthetic or recombinant methods) that are commonly found in cells and tissues. Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

"Biocompatible": The term "biocompatible", as used herein is intended to describe materials that do not elicit a substantial detrimental response in vivo.

"Biodegradable": As used herein, "biodegradable" polymers are polymers that degrade fully under physiological or endosomal conditions. In preferred embodiments, the polymers and biodegradation byproducts are biocompatible. Biodegradable polymers are not necessarily hydrolytically degradable and may require enzymatic action to fully degrade.

"Degradation": The phrase "degradation", as used herein, relates to the cleavage of a covalent polymer backbone. Full degradation of a polymer breaks the polymer down to monomeric species.

"Endosomal conditions": The phrase "endosomal conditions", as used herein, relates to the range of chemical (e.g., pH, ionic strength) and biochemical (e.g., enzyme concentrations) conditions likely to be encountered within endosomal vesicles. For most endosomal vesicles, the endosomal pH ranges from about 5.0 to 6.5.

"Hydrolytically degradable": As used herein, "hydrolytically degradable" polymers are polymers that degrade fully in the sole presence of water. In preferred embodiments, the polymers and hydrolytic degradation byproducts are biocompatible. As used herein, the term "non-hydrolytically degradable" refers to polymers that do not fully degrade in the sole presence of water.

"Physiological conditions": The phrase "physiological conditions", as used herein, relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4.

"Polyelectrolyte" or "polyion": The terms "polyelectrolyte" or "polyion", as used herein, refer to a polymer which under some set of conditions (e.g., physiological conditions) has a net positive or negative charge. Polycations have a net positive charge and polyanions have a net negative charge. The net charge of a given polyelectrolyte or polyion may depend on the surrounding chemical conditions, e.g., on the pH.

"Polynucleotide", "nucleic acid", or "oligonucleotide": The terms "polynucleotide", "nucleic acid", or "oligonucleotide" refer to a polymer of nucleotides. The terms "polynucleotide", "nucleic acid", and "oligonucleotide", may be used interchangeably. Typically, a polynucleotide comprises at least three nucleotides. DNAs and RNAs are polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

"Polypeptide", "peptide", or "protein": According to the present invention, a "polypeptide", "peptide", or "protein" comprises a string of at least three amino acids linked together by peptide bonds. The terms "polypeptide", "peptide", and "protein", may be used interchangeably. Peptide may refer to an individual peptide or a collection of peptides. Inventive peptides preferably contain only natural amino acids, although non-natural amino acids (i.e., compounds that do not occur in nature but that can be incorporated into a polypeptide chain; see, for example, http://www.cco.caltech.edu/~dadgrp/Unnatstruct.gif, which displays structures of non-natural amino acids that have been successfully incorporated into functional ion channels) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

"Polysaccharide", "carbohydrate" or "oligosaccharide": The terms "polysaccharide", "carbohydrate", or "oligosaccharide" refer to a polymer of sugars. The terms "polysaccharide", "carbohydrate", and "oligosaccharide", may be used interchangeably. Typically, a polysaccharide comprises at least three sugars. The polymer may include natural sugars (e.g., glucose, fructose, galactose, mannose, arabinose, ribose, and xylose) and/or modified sugars (e.g., 2'-fluororibose, 2'-deoxyribose, and hexose).

"Small molecule": As used herein, the term "small molecule" is used to refer to molecules, whether naturally-occurring or artificially created (e.g., via chemical synthesis), that have a relatively low molecular weight. Typically, small molecules are monomeric and have a molecular weight of less than about 1500 g/mol. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§ 330.5, 331 through 361, and 440 through 460; drugs for veterinary use listed by the FDA under 21 C.F.R. §§ 500 through 589, incorporated herein by reference, are all considered acceptable for use in accordance with the present invention.

"Bioactive agents": As used herein, "bioactive agents" is used to refer to compounds or entities that alter, inhibit, activate, or otherwise affect biological or chemical events. For example, bioactive agents may include, but are not limited to, anti-AIDS substances, anti-cancer substances, antibiotics, immunosuppressants, anti-viral substances, enzyme inhibitors, neurotoxins, opioids, hypnotics, antihistamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, antidepressants, anti-psychotic substances, anti-emetics, and imaging agents. In certain embodiments, the bioactive agent is a drug.

A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996, and the United States Pharmacopeia-25/National Formulary-20, published by the United States Pharmcopeial Convention, Inc., Rockville Md., 2001, all of which are incorporated herein by reference.

ACRONYMS

The following acronyms are used herein: "SPS" is poly (styrene sulfonate), "PAA" is poly(acrylic acid), "LPEI" is linear poly(ethylene imine), "PDAC" is poly(diallyl dimethyl ammonium chloride), "PAH" is poly(allylamine hydrochloride), and "PAZO" is the azobenzene functionalized polymer poly {1-[4-(3-carboxy-4-hydroxyphenylazo) benzensulfonamido]-1,2-ethanediyl}.

DESCRIPTION OF THE DRAWING

The invention is described with reference to several figures of the drawing, in which.

DETAILED DESCRIPTION

The present invention provides a method for the gradual and controlled release of one or more entities from decomposable thin films. The decomposition is characterized by the substantially sequential degradation of at least a portion of the polyelectrolyte layers that make up the thin films. The degradation may be at least partially hydrolytic, at least partially enzymatic, at least partially thermal, and/or at least partially photolytic.

Several groups have reported the deposition of polyelectrolytes onto microcrystalline templates to yield semi-permeable films that release compounds via diffusion (see Qiu et al., *Langmuir* 17:5375, 2001 and Antipov et al., *J. Phys. Chem. B* 105:2281, 2001). However, while multi-layer films are permeable to small molecules (e.g., ibuprofen and fluorescein), they are much less permeable to molecules with molecular weights larger than 4 kDa (see Sukhorukov et al., *J. Phys. Chem. B* 103:6434, 1999), and are therefore less well-suited to the diffusive release of biomolecules, e.g., DNA, RNA, and proteins.

Recent work has also demonstrated that certain multi-layer films can be "deconstructed" at high salt concentrations (see Dubas and Schlenoff, *Macromolecules* 34:3736, 2001). As described by Dubas and Schlenoff, at high salt concentrations the free ions compete for the charged groups of the polyelectrolytes and hence weaken intermolecular interactions within the film, thereby causing it to fall apart. This concept has been extended to the fabrication of films that release DNA in the presence of salt (see Schüler and Caruso, *Biomacromolecules* 2:921, 2001). Unfortunately, deconstruction occurs under conditions of high ionic strength (e.g., salt concentrations of 0.6–5 M), and is therefore not well-suited to the release of molecules under physiological conditions.

Figure 1:
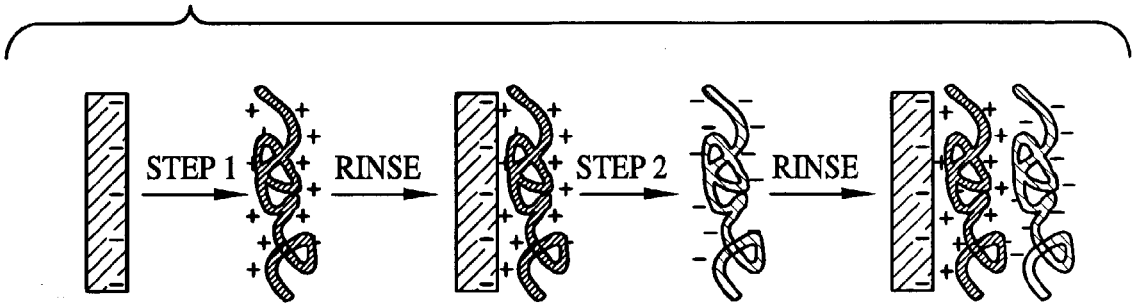
FIG. 1 is a schematic illustrating the construction of a thin film via layer-by-layer deposition of polyelectrolytes on a charged substrate.
Figure 2:
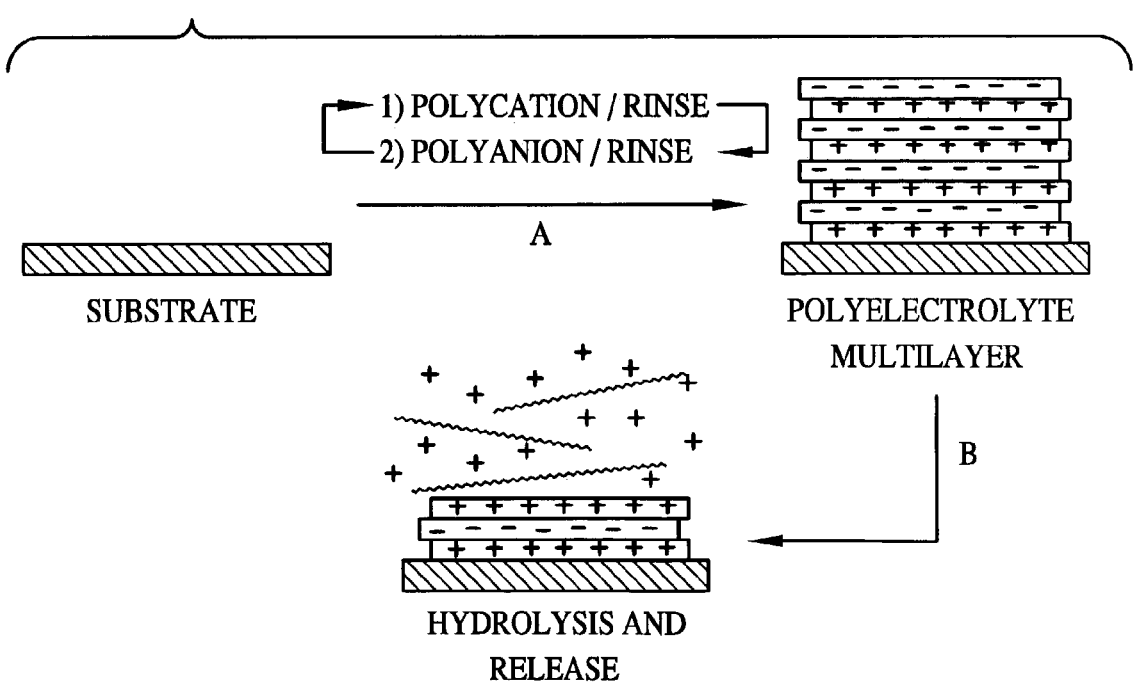
FIG. 2 is a schematic illustrating the construction and decomposition of a thin film according to one embodiment of the invention by (A) layer-by-layer deposition of alternating polyanionic and polycationic layers and (B) degradation of polycationic layers and release of polyanionic components.

In certain embodiments of the instant invention, the released entities are structural polyelectrolyte components of the inventive films. One such embodiment of the invention is illustrated in FIG. 2. In step A of this embodiment, the thin film is deposited on a substrate via layer-by-layer assembly as depicted in FIG. 1. The thin film includes a plurality of alternating polyanionic and polycationic layers. The polycationic layers include a degradable polycation. In step B, the thin film is exposed to a degrading medium (e.g., intracellular fluid), whereupon the polycationic layers degrade and the polyanionic layers delaminate sequentially from the surface toward the substrate. The component polyanions of the exposed polyanionic layers are thus gradually and controllably released from the surface of the thin film. In preferred embodiments, the released polyanions are biomolecules, for example, DNA molecules. If the thin film is to be disposed in vivo, the polycations and their degradation byproducts are preferably biocompatible. It will be appreciated that the roles of the two layers of the thin film can be reversed. In such embodiments, the polyanionic layers include a degradable polyanion and the polycationic layers may include, for example, a polycationic protein. Alternatively, both the polycationic and polyanionic layers may both include degradable polyelectrolytes.

A variety of materials can be used as substrates of the present invention such as, but not limited to, metals, e.g., gold, silver, platinum, and aluminum; metal-coated materials; metal oxides; plastics; ceramics; silicon; glasses; mica; graphite; hydrogels; polymers such as polyamides, polyphosphazenes, polypropylfumarates, polyethers, polyacetals, polycyanoacrylates, polyurethanes, polycarbonates, polyanhydrides, polyorthoesters, polyhydroxyacids, polyacrylates, ethylene vinyl acetate polymers and other cellulose acetates, polystyrenes, poly(vinyl chloride), poly(vinyl fluoride), poly(vinylimidazole), poly(vinyl alcohol), poly (ethylene terephthalate), polyesters, polyureas, polypropylene, polymethacrylate, polyethylene, poly(ethylene oxide)s and chlorosulphonated polyolefins; and combinations thereof. For example, a substrate of one material may be coated with a second material, or two materials may be combined to form a composite.

It will be appreciated that materials with an inherently charged surface are particularly attractive substrates for LBL assembly of an inventive thin film. Alternatively, a range of methods are known in the art that can be used to charge the surface of a material, including but not limited to plasma processing, corona processing, flame processing, and chemical processing, e.g., etching, micro-contact printing, and chemical modification. For example, plastics can be used as substrates, particularly if they have been chemically modified to present polar or charged functional groups on the surface. Additionally or alternatively, substrates can be primed with specific polyelectrolyte bilayers such as, but not limited to, LPEI/SPS, PDAC/SPS, PAH/SPS, LPEI/PAA, PDAC/PAA, and PAH/PAA bilayers, that form readily on weakly charged surfaces and occasionally on neutral surfaces. It will be appreciated that primer layers provide a uniform surface layer for further LBL assembly and are therefore particularly well suited to applications that require the deposition of a uniform thin film on a substrate that includes a range of materials on its surface, e.g., an implant or a complex tissue engineering construct.

Any degradable polyelectrolyte can be used in a thin film of the present invention, including, but not limited to, hydrolytically degradable, biodegradable, thermally degradable, and photolytically degradable polyelectrolytes. Hydrolytically degradable polymers known in the art include for example, certain polyesters, polyanhydrides, polyorthoesters, polyphosphazenes, and polyphosphoesters. Biodegradable polymers known in the art, include, for example, certain polyhydroxyacids, polypropylfumerates, polycaprolactones, polyamides, poly(amino acids), polyacetals, polyethers, biodegradable polycyanoacrylates, biodegradable polyurethanes and polysaccharides. For example, specific biodegradable polymers that may be used in the present invention include but are not limited to polylysine, poly (lactic acid) (PLA), poly(glycolic acid) (PGA), poly(caprolactone) (PCL), poly(lactide-co-glycolide) (PLG), poly(lactide-co-caprolactone) (PLC), and poly(glycolide-co-caprolactone) (PGC). Those skilled in the art will recognize that this is an exemplary, not comprehensive, list of biodegradable polymers. The properties of these and other polymers and methods for preparing them are further described in the art. See, for example, U.S. Pat. Nos. 6,123,727; 5,804,178; 5,770,417; 5,736,372; 5,716,404 to Vacanti; U.S. Pat. Nos. 6,095,148; 5,837,752 to Shastri; U.S. Pat. No. 5,902,599 to Anseth; U.S. Pat. Nos. 5,696,175; 5,514,378; 5,512,600 to Mikos; U.S. Pat. No. 5,399,665 to Barrera; U.S. Pat. No. 5,019,379 to Domb; U.S. Pat. No. 5,010,167 to Ron; U.S. Pat. Nos. 4,806,621; 4,638,045 to Kohn; and U.S. Pat. No. 4,946,929 to d'Amore; see also Wang et al., *J. Am. Chem. Soc.* 123:9480, 2001; Lim et al., *J. Am. Chem. Soc.* 123:2460, 2001; Langer, *Acc. Chem. Res.* 33:94, 2000; Langer, *J. Control Release* 62:7, 1999; and Uhrich et al., *Chem. Rev.* 99:3181, 1999. Of course, co-polymers, mixtures, and adducts of these polymers may also be employed.

The anionic polyelectrolytes are preferably degradable polymers with anionic groups distributed along the polymer backbone. The anionic groups, which may include carboxylate, sulfonate, sulphate, phosphate, nitrate, or other negatively charged ionizable groupings, may be disposed upon groups pendant from the backbone or may be incorporated in the backbone itself. The cationic polyelectrolytes are preferably degradable polymers with cationic groups distributed along the polymer backbone. The cationic groups, which may include protonated amine, quaternary ammonium or phosphonium derived functions, may be disposed in side groups pendant from the backbone, may be attached to the backbone directly, or can be incorporated in the backbone itself.

For example, a range of hydrolytically degradable amine containing polyesters bearing cationic side chains have recently been developed (Putnam et al. *Macromolecules* 32:3658–3662, 1999; Barrera et al. *J. Am. Chem. Soc.* 115:11010–11011, 1993; Kwon et al. *Macromolecules* 22:3250–3255, 1989; Lim et al. *J. Am. Chem. Soc.* 121: 5633–5639, 1999; Zhou et al. *Macromolecules* 23:3399–3406, 1990; each of which is incorporated herein by reference). Examples of these polyesters include poly(L-lactide-co-L-lysine) (Barrera et al. *J. Am. Chem. Soc.* 115: 11010–11011, 1993; incorporated herein by reference), poly (serine ester) (Zhou et al. *Macromolecules* 23:3399–3406, 1990; which is incorporated herein by reference), poly(4-hydroxy-L-proline ester) (Putnam et al. *Macromolecules* 32:3658–3662, 1999.; Lim et al. *J. Am. Chem. Soc.* 121: 5633–5639, 1999; each of which is incorporated herein by reference), and more recently, poly[$\alpha$-(4-aminobutyl)-L-glycolic acid].

In addition, poly($\beta$-amino ester)s, prepared from the conjugate addition of primary or secondary amines to diacrylates, are suitable for use with the invention. Typically, poly($\beta$-amino ester)s have one or more tertiary amines in the backbone of the polymer, preferably one or two per repeating backbone unit. Alternatively, a co-polymer may be used in which one of the components is a poly($\beta$-amino ester). Poly($\beta$-amino ester)s are described in U.S. application Ser. No. 09/969,431, filed Oct. 2, 2001, entitled "Biodegradable poly($\beta$-amino esters) and uses thereof" and Lynn et al., *J. Am. Chem. Soc.* 122:10761–10768, 2000, the entire contents of both of which are incorporated herein by reference.

Figure 3:
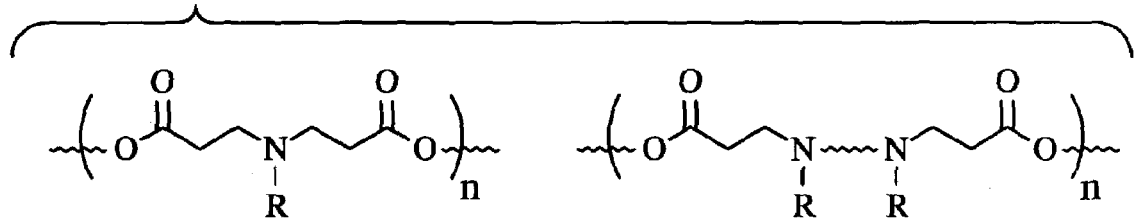
FIG. 3 depicts the chemical structure of exemplary hydrolytically degradable polycations for the fabrication of a decomposable thin film.

Exemplary poly($\beta$-amino ester)s are shown in FIG. 3. Exemplary R groups include hydrogen, branched and unbranched alkyl, branched and unbranched alkenyl, branched and unbranched alkynyl, aryl, halogen, hydroxyl, alkoxy, carbamoyl, carboxyl ester, carbonyldioxyl, amide, thiohydroxyl, alkylthioether, amino, alkylamino, dialkylamino, trialkylamino, cyano, ureido, a substituted alkanoyl group, cyclic, cyclic aromatic, heterocyclic, and aromatic heterocyclic groups, each of which may be substituted with at least one substituent selected from the group consisting of branched and unbranched alkyl, branched and unbranched alkenyl, branched and unbranched alkynyl, amino, alkylamino, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiol groups.

Exemplary linker groups A and B include carbon chains of 1 to 30 carbon atoms, heteroatom-containing carbon chains of 1 to 30 atoms, and carbon chains and heteroatom-containing carbon chains with at least one substituent selected from the group consisting of branched and unbranched alkyl, branched and unbranched alkenyl, branched and unbranched alkynyl, amino, alkylamino, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiol groups. The polymer preferably has between 5 and 10,000 repeat units.

Alternatively, zwitterionic polyelectrolytes may be used. Such polyelectrolytes may have both anionic and cationic groups incorporated into the backbone or covalently attached to the backbone as part of a pendant group. Such polymers may be neutrally charged at one pH, positively charged at another pH, and negatively charged at a third pH. For example, a film may be deposited by LBL deposition using dip coating in solutions of a first pH at which one layer is anionic and a second layer is cationic. If the film is put into a solution having a second different pH, then the first layer may be rendered cationic while the second layer is rendered anionic, thereby changing the charges on those layers.

In certain embodiments, the LBL assembly of inventive films may involve a series of dip coating steps in which the substrate is dipped in alternating polycationic and polyanionic solutions (see FIG. 1). Additionally or alternatively, it will be appreciated that deposition of alternating polycationic and polyanionic layers may also be achieved by spray coating, brush coating, roll coating, spin casting, or combinations thereof.

Figure 4:
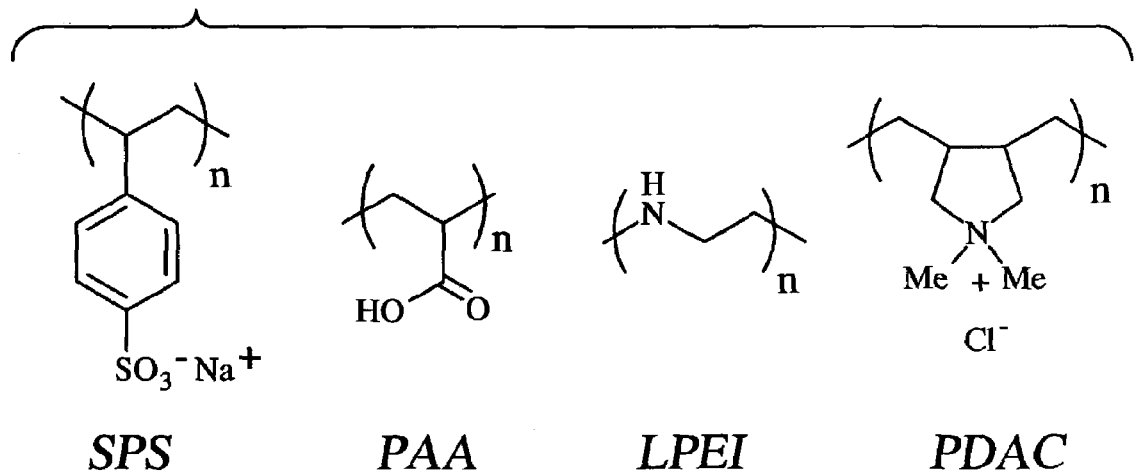
FIG. 4 depicts the chemical structure of exemplary non-degradable polyanions and polycations for the fabrication of a thin film according to one embodiment of this invention.

The composition of the polyanionic and polycationic layers can be fine-tuned to adjust the degradation rate of each layer within the film. For example, the degradation rate of hydrolytically degradable polyelectrolyte layers can be decreased by associating hydrophobic polymers such as hydrocarbons and lipids with one or more of the layers. Alternatively, the polyelectrolyte layers may be rendered more hydrophilic to increase their hydrolytic degradation rate. In certain embodiments, the degradation rate of a given layer can be adjusted by including a mixture of polyelectrolytes that degrade at different rates or under different conditions. In other embodiments, the polyanionic and/or polycationic layers may include a mixture of degradable and non-degradable polyelectrolytes. Any non-degradable polyelectrolyte can be used with the present invention. Exemplary non-degradable polyelectrolytes that could be used in thin films of the present invention are shown in FIG. 4 and include poly(styrene sulfonate) (SPS), poly(acrylic acid) (PAA), linear poly(ethylene imine) (LPEI), poly(diallyldimethyl ammonium chloride) (PDAC), and poly(allylamine hydrochloride) (PAH).

Alternatively or additionally, the degradation rate may be fine-tuned by associating or mixing non-biodegradable, yet biocompatible polymers (polyionic or non-polyionic) with one or more of the polyanionic and/or polycationic layers. Suitable non-biodegradable, yet biocompatible polymers are well known in the art and include polystyrenes, certain polyesters, non-biodegradable polyurethanes, polyureas, poly(ethylene vinyl acetate), polypropylene, polymethacrylate, polyethylene, polycarbonates, and poly (ethylene oxide)s.

Furthermore, because the thin film is produced in a layer-by-layer fashion, the composition of individual layers may be varied to tailor the degradation rate of various portions of the film. For example, the upper layers of the film, closer to the surface, may be adjusted to degrade faster than the layers of the film closer to the substrate, or vice versa. Depending on the thickness of the film, the degradation rate within the film may be varied cyclically (e.g., for periodic release). Additionally or alternatively, the upper layers of the film, closer to the surface, may be adjusted to degrade under a first set of conditions (e.g., endosomal conditions) while the layers of the film that are closer to the substrate are adjusted to degrade under a second set of conditions (e.g., physiological conditions).

Figure 5:
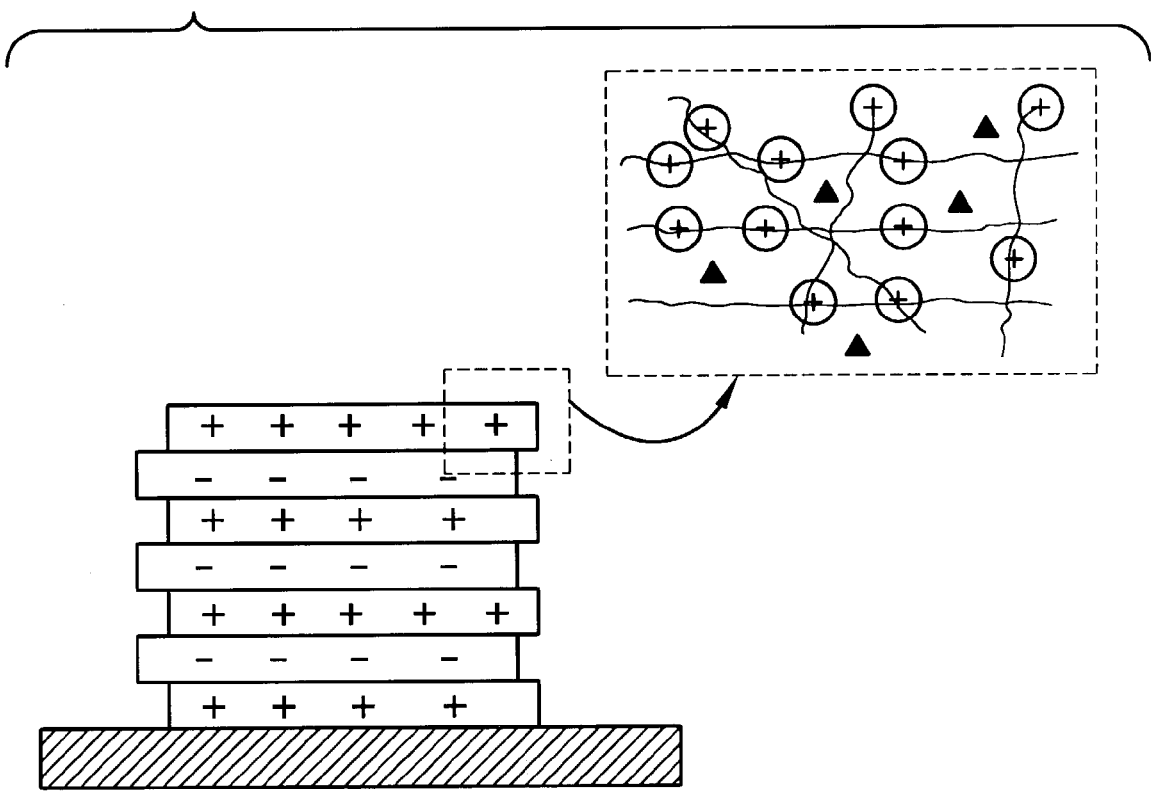
FIG. 5 is a schematic illustrating entities (shown as black triangles), e.g., biomolecules or small molecules that are non-covalently associated with polycations of a thin film according to one embodiment of the invention.
Figure 6:
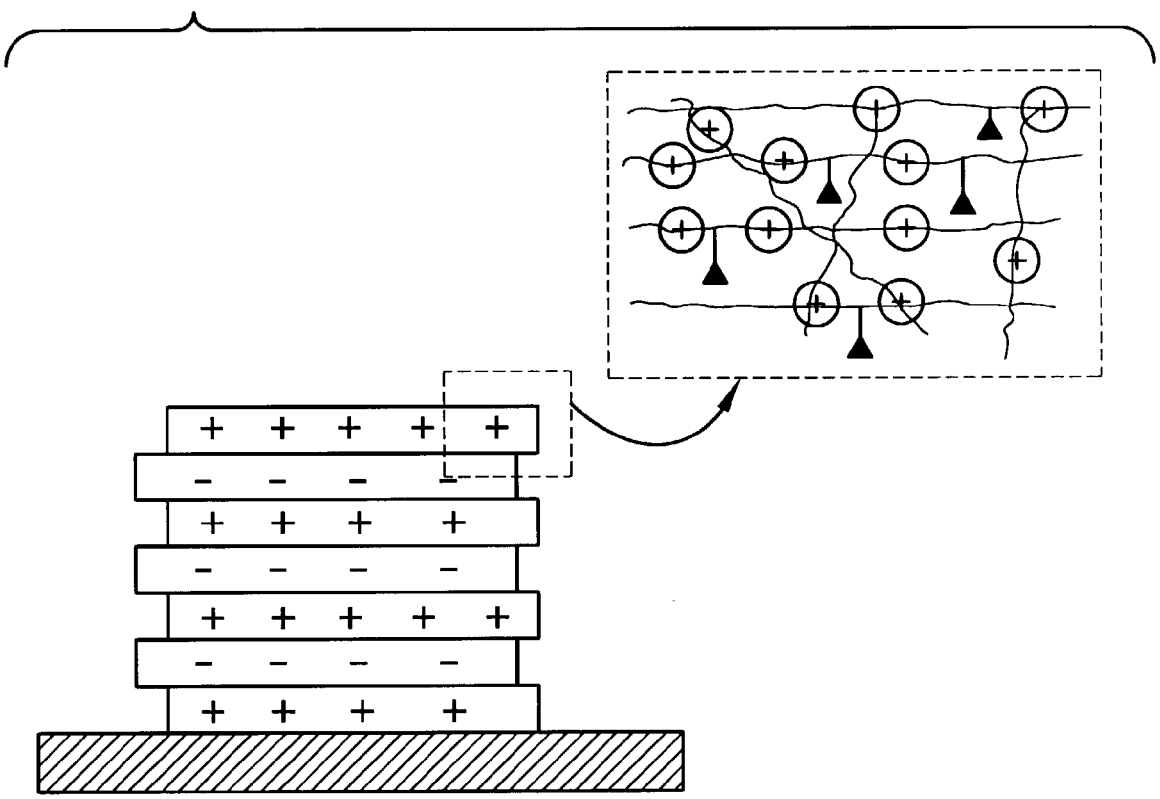
FIG. 6 is a schematic illustrating entities (shown as black triangles), e.g., biomolecules or small molecules that are covalently associated with polycations of a thin film according to one embodiment of the invention.

The released entity need not act as a structural component of the film (see FIGS. 5 and 6). As noted above, polyelectrolytes may be associated or mixed with polymeric or non-polymeric moieties to regulate the degradation rate. In addition, neutral, zwitterionic, or charged biomolecules, small molecules, or bioactive agents may be associated or mixed with a polycation or polyanion and incorporated into a layer. For example, the charged atoms on a zwitterionic molecule may facilitate electrostatic interactions with both the polyanionic and polycationic layers. A zwitterionic biomolecule, small molecule, or bioactive agent may be combined in solution with the polyelectrolytes for one of the layers or placed in a separate solution to form a "sandwich" between two layers. When the thin film degrades, the biomolecule, small molecule, or bioactive agent will be released. Alternatively, a biomolecule, small molecule, or bioactive agent may be associated with a polyelectrolyte under conditions which facilitate a strong interaction between the molecule and the polyelectrolyte, while the medium in which the biomolecule, small molecule, or bioactive agent is released is one which competes with the polyelectrolyte for the biomolecule, small molecule, or bioactive agent, thereby decreasing the strength of the interaction with the polyelectrolyte.

The composition of the various layers may be adjusted to release different entities as the thin film degrades. For example, a thin film may be designed to release a chemotactic factor tailored to attract cells to an implant site for a specified number of layers, followed by a growth factor tailored to stimulate a desired metabolic or proliferative activity in cells now at the implant site.

It will be appreciated that in preparing a thin film that degrades with a desired rate and profile one may need to test various thin film compositions experimentally. The degradation rates and profiles of inventive thin films can, for example, be investigated using a variety of known techniques, including ellipsometry, dynamic light scattering (DLS), zeta-potential analysis, quartz crystal microbalance (QCM), and atomic force microscopy (AFM). The QCM method is particularly attractive since it can be used with rough films and allows continuous monitoring without removal of the thin films from the degradation milieu. AFM can be also used to monitor changes in the multi-layer surface morphology as a function of degradation.

Figure 7:
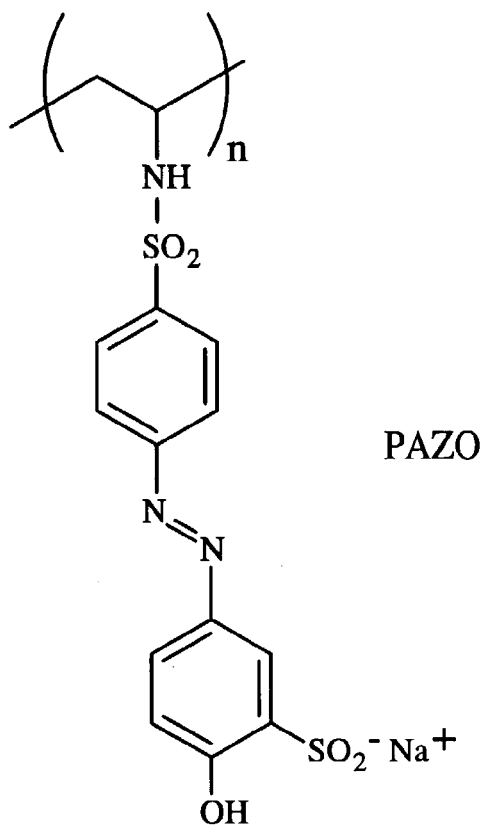
FIG. 7 depicts the chemical structure of PAZO, an azobenzene functionalized photochromic polyanion.

Additionally or alternatively, one may choose to monitor the rate at which a non-degradable structural polymer, biomolecule, small molecule, or bioactive agent is released from the thin film. If the released entity absorbs or emits light in an uncrowded region of the ultraviolet or visible electromagnetic spectrum, one could measure the rate of release by UV-visible spectroscopy. It will be appreciated that a variety of synthetic and recombinant techniques exist that allow one to attach a light absorbing or emitting group, e.g., a fluorescent group or a dye to a polymer or small molecule that lacks such functionality. Alternatively, one could incorporate a model chromic compound, e.g., the commercially available photochromic polyanion PAZO (see FIG. 7), into a range of thin films for this purpose.

The thin film may also be used to create a degradable substrate for cell seeding and culture. Some cells, for example, chondrocytes, proliferate better when deposited on a substrate to which they can attach. However, to use these cells in other applications, they may need to be separated from the substrate. Cells may be deposited on the surface of a multi-layer thin film and maintained in vitro. As the thin film degrades, the cells are released into the surrounding medium, freeing them for seeding onto tissue engineering matrices or for analysis. Integrins and cell adhesion sequences (e.g., the RGD sequence) may be included in the top layer or layers of the film to facilitate cell adhesion. Integrins are part of a large family of cell adhesion receptors which are involved in cell-extracellular matrix and cell-cell interactions. The RGD sequence, present in proteins such as fibronectin, has been shown to be active in promoting cell adhesion and proliferation (see Massia et al., *J. Cell. Biol.* 114:1089, 1991).

The thin films may include electroactive polymers. In the presence or absence of a voltage, conductive polymers may enhance the proliferation and metabolism of cells deposited thereon (U.S. Pat. No. 6,095,148, issued Aug. 1, 2000, and U.S. Pat. No. 6,190,893, issued Feb. 20, 2001). The voltage may be an externally applied voltage. Alternatively, a voltage may be applied by native tissue, for example, nerve. Bone is piezoelectric, and physiologic loading will generate a potential across a film implanted therein. Exemplary electroactive polymers include, but are not limited to, polypyrrole, poly(p-phenylene), poly(p-phenylene vinylene), polythiophene, polyaniline, polyporphyrin, polyheme, and derivatives thereof. These polymers may be derivatized. For example, hydrocarbon groups, methoxy, cyano, phenyl, alkoxy, amino, and halides may be added to aromatic groups in the polymer, and except for halides (which would lead to the production of poly(phenylene acetylene)), to the non-aromatic carbons. Of course, if the film is intended for biological applications, the resulting derivative should be biocompatible.

The invention can employ a wide range of cell types and is not limited to any specific cell type. Examples of cell types that may be used include but are not limited to bone or cartilage forming cells such as chondrocytes and fibroblasts, other connective tissue cells, epithelial cells, endothelial cells, blood vessel cells, cancer cells, organ cells such as hepatocytes, islet cells, kidney cells, intestinal cells, and lymphocytes, smooth muscle cells, skeletal muscle cells, heart muscle cells, nerve cells, and stem cells such as human embryonic stem cells or mesenchymal stem cells.

In another embodiment, the thin film may encapsulate a decomposable substrate (e.g., a drug nano- or micro-crystal). Additionally or alternatively, the thin film may be exploited to regulate diffusion of the substrate into the surrounding medium. In certain embodiments, particularly for drug delivery, it may be desirable to target an encapsulated substrate to a particular cell or tissue. A variety of agents that can direct an encapsulated substrate to particular cells are known in the art (see, for example, Cotten et al., *Methods Enzym.* 217:618, 1993). Examples of useful targeting agents include, but are in no way limited to, low-density lipoproteins (LDLs), transferrin, asiaglycoproteins, gp120 envelope protein of the human immunodeficiency virus (HIV), toxins, antibodies, and carbohydrates. Certain preferred encapsulated substrates of the present invention include one or more targeting agents that are associated with polyelectrolyte components of the inventive thin film and/or with the entity to be released.

The substrate geometry may be manipulated to deposit films having a variety of shapes. For example, films may be deposited on particles, tubes, or spheres to facilitate a more uniform release distribution. Films may be deposited on strands such as sutures to release factors such as analgesics or antibiotics at a surgical site. Alternatively, these films may be deposited onto capillary networks or tissue engineering constructs. For example, a thin film deposited on a three-dimensional tissue engineering construct may be used to attract cells to a newly implanted construct and then to promote specific metabolic or proliferative activity.

Figure 8:
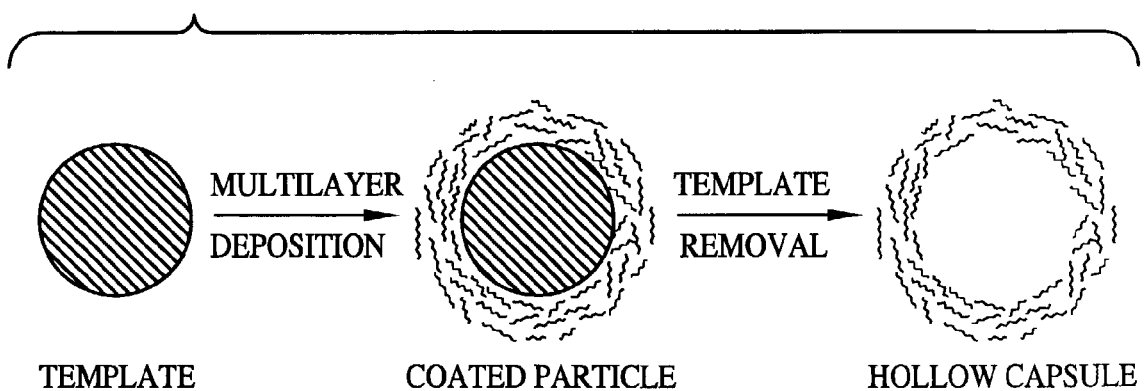
FIG. 8 is a schematic illustrating the deposition of a decomposable thin film on a particulate template and construction of a decomposable hollow thin film microcapsule by dissolution of the template.
Figure 9:
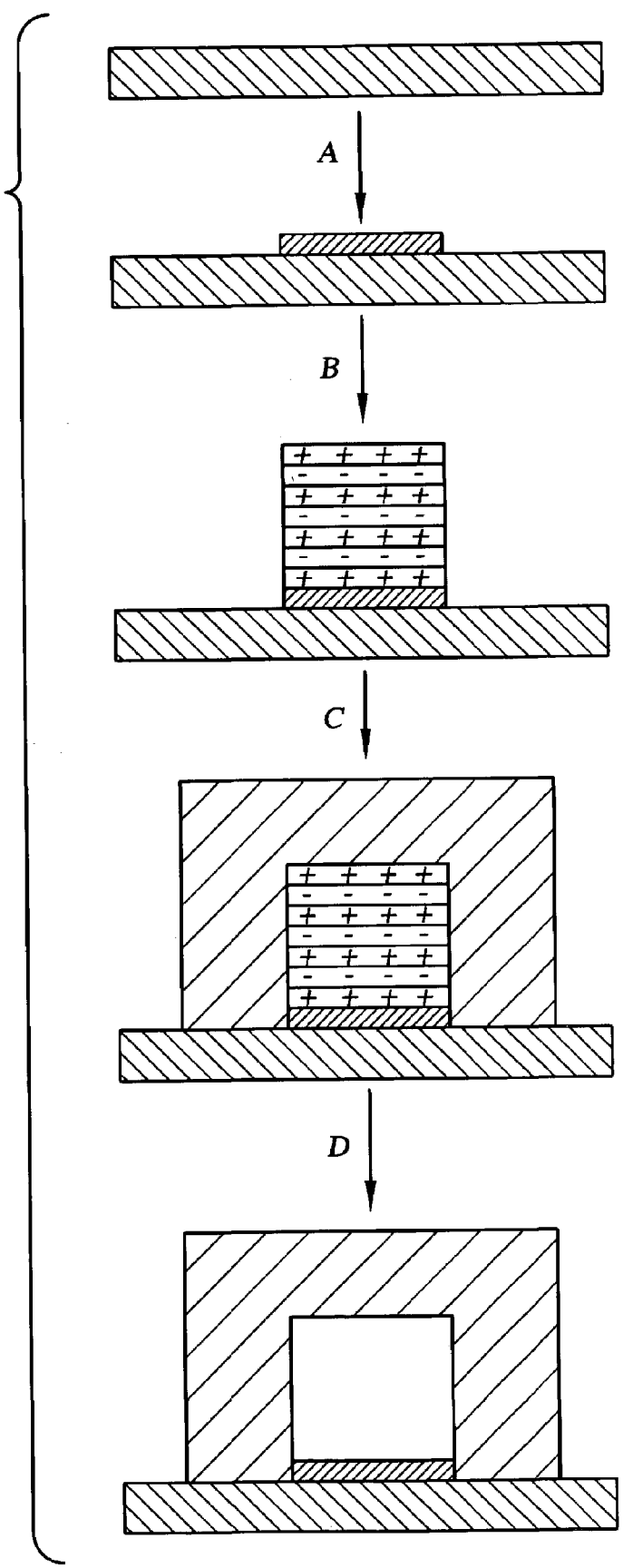
FIG. 9 is a schematic illustrating the construction of a tunnel-like microstructure according to one embodiment of the invention by (A) deposition of an ionic or polar self-assembled monolayer (SAM), e.g., by micro-contact printing, (B) layer-by-layer deposition of a decomposable thin film, (C) flooding of the substrate with a non-degradable material, and (D) decomposition of the thin film.

The methods of the invention may also be used to create three-dimensional microstructures. For example, the thin film may be deposited on a substrate that can be dissolved to leave a hollow shell of the thin film (see FIG. 8). Alternatively, multi-layers may be deposited having regions that are more and less degradable. Degradation of the degradable portions leaves a three-dimensional microstructure (see FIG. 9). In a first step, the surface of a substrate is divided into regions in which LBL deposition of an inventive thin film is more or less favorable (see FIG. 9, step A). In one embodiment, a pattern of self-assembled monolayers (SAMs) is deposited on a substrate surface by microcontact printing (see, for example, U.S. Pat. No. 5,512,131 to Kumar et al., see also Kumar et al., Langmuir 10:1498, 1994; Jiang and Hammond, Langmuir, 16:8501, 2000; Clark et al., Supramolecular Science 4:141, 1997; and Hammond and Whitesides, Macromolecules 28:7569, 1995). In preferred embodiments, the substrate surface is neutral and the exposed surface of the deposited SAMs is polar or ionic (i.e., charged). A variety of polymers with polar or ionic head groups are known in the art of self-assembled monolayers. In another embodiment, a uniform coating of a polymer is deposited on a substrate, and that coating is transformed into a patterned layer by means of photolithography. Other embodiments are also contemplated in which the substrate surface is selectively exposed to plasmas, various forms of electromagnetic radiation, or to electron beams. In yet other embodiments, the substrate may possess the desired surface characteristics by virtue of its inherent composition. For example, the substrate may be a composite in which different regions of the surface have differing compositions, and thus different affinities for the polyelectrolyte to be deposited.

In a second step, polyelectrolyte layers of alternating charge are deposited by LBL on receptive regions of the surface (see FIG. 9, step B) as described for a homogeneous surface above and selective regions in Jiang and Hammond, Langmuir, 16:8501, 2000; Clark et al., Supramolecular Science 4:141, 1997; and Hammond and Whitesides, Macromolecules 28:7569, 1995. The surface is subsequently flooded with a non-degradable polymer (see FIG. 9, step C) and placed in a medium wherein at least a portion of the polyelectrolyte layers degrade, thereby creating a three-dimensional "tunnel-like" structure that reflects the pattern on the original surface (see FIG. 9, step D). It will be appreciated that more complex microstructures could be created based on these simple principles (e.g., by depositing SAMs with different electrostatic character in different regions of a substrate surface and/or by iterative additions of subsequent structures above the deposited non-degradable polymer).

EXAMPLES

Materials and Methods

Figure 10:
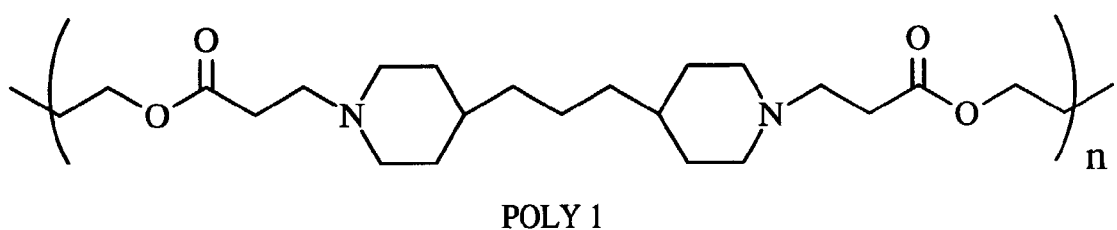
FIG. 10 depicts the chemical structure of Polymer 1 (Poly 1), a hydrolytically degradable poly($\beta$-amino ester)

Polymers: The poly($\beta$-amino ester) "Poly 1" (FIG. 10) was selected for use in initial experiments based on the relatively slow degradation rate of this polymer at acidic pH ($t_{1/2}$>10 h at pH=5.1, 37° C.) (Lynn, D. M., et al., *J. Am. Chem. Soc.*, 122:10761–10768, 2000). As Poly 1 has also been shown to form electrostatic complexes with polyanions such as DNA in solution, we hypothesized that it would readily absorb to negatively-charged surfaces and model polyanions such as poly(styrene sulfonate) (SPS) and poly(acrylic acid) (PAA) commonly used for LBL assembly.

Poly(sodium 4-styrenesulfonate), "SPS", MW~70,000 and highly polymerized calf thymus DNA were obtained from Sigma-Aldrich, St Louis, Mo. Linear poly(ethylene imine), "LPEI", MW~25,000, poly(dimethyldiallylammonium chloride) "PDAC", MW~240,000) and poly(acrylic acid), "PAA", MW~90,000 were obtained from Polysciences, Warrington, Pa. Poly 1 (see FIG. 10, MW~10,000), was synthesized as described in Lynn et al., *J. Am. Chem. Soc.* 122:10761–10768, 2000, the contents of which are hereby incorporated by reference. All polyelectrolytes were used without further purification or filtration, with the exception of Poly 1. Poly 1 solutions were filtered using a 0.45 µm membrane syringe filter prior to use. All polymer solutions used for deposition were pH adjusted to 5.1 with a concentration of 5 mM for Poly 1 and 20 mM for all other polyelectrolytes (calculations based on monomer unit). Poly 1 was dissolved in a 100 mM sodium acetate buffer. Other solutions were prepared with deionized water and the pH was adjusted using sodium hydroxide and hydrochloric acid.

Other Chemicals: The water used for all experimental procedures was obtained from a Milli-Q Reagent Water System (Millipore, Bedford, Mass.) at 18.2 MΩcm. For degradation, PBS buffer pH 7.4 (0.1 mM $Na_2HPO_4$, 150 mM NaCl, 0.027 mM KCl), 100 mM sodium acetate buffer pH 5.1 and TAE buffer pH 8.3 (0.4 mM Tris-acetate and 0.01 mM EDTA) were used. All buffered solutions used for decomposition were salt (NaCl) adjusted to 150 mM to maintain a physiologically relevant salt concentration.

Polyelectrolyte Deposition: Silicon substrates were cut to approximately 1 cm×2 cm and rinsed with acetone and ethanol. They were then dried using a nitrogen stream and plasma etched to remove any organic materials and to charge the surface with oxygen radicals. Glass substrates underwent the same procedure. The optical constants (Ns and Ks) for the substrates were then obtained from a Gaertner Variable Angle Ellipsometer (6328 nm, incident angle=70°). Data were collected and processed using the Gaertner Ellipsometry Measurement Program (GEMP), Version 1.2 software package.

Substrates were then placed in a Carl Zeiss HMS Series Programmable Slide Stainer (Carl Zeiss, Thornwood, N.Y.) where ten precursor bilayers (ca. 100–200 Å) of LPEI/SPS or PDAC/PAA were deposited, terminating with the polyanion monolayer. This was done to assure a strong known net charge on the surface. After measuring the film thickness using ellipsometry, ten bilayers of Poly 1/SPS or Poly 1/PAA were deposited on top of the original film.

The slide stainer was programmed to submerge the substrates in the polycation solution for five minutes and then to rinse the substrates in two successive deionized water baths. The first rinse was of one minute and the following of two minutes and thirty seconds. The substrates were then submerged five more minutes in the polyanion solution and then rinsed in the same manner. After one bilayer was deposited, the substrates were ultra sonicated for four minutes and thirty seconds. This ultra sonication step is believed to improve the surface's topography. The program was then cycled to obtain the desirable bilayers of film.

After deposition, films were dried with nitrogen to remove visible drops of solution from the surface before ellipsometry or profilometry was performed. Multilayers incorporating poly 1 were removed from aqueous water baths immediately after final layers were deposited, dried under a stream of dry nitrogen, placed in a vacuum dessicator and dried overnight to minimize degradation due to incorporated water. Root mean square roughness was determined using a Tencor Corporation KLA Model P10 Surface Profilometer with a 2 um stylus. Reflective FTIR spectra were recorded using a Nicolet Magna-IR 550 Series II Spectrometer. Substrates to be used for reflective FTIR analysis were coated with a thin layer of gold using a thermal evaporator. Decomposition experiments were performed by submerging the substrates in buffered solutions at room temperature or 37° C. and taking measurements by ellipsometry or UV-visible spectroscopy at desired time intervals. The thickness of each sample was determined by ellipsometry at nine different predetermined locations on the substrate surface (measured in triplicate), and the sample was returned to the buffer solution.

Results and Discussion

Figure 11:
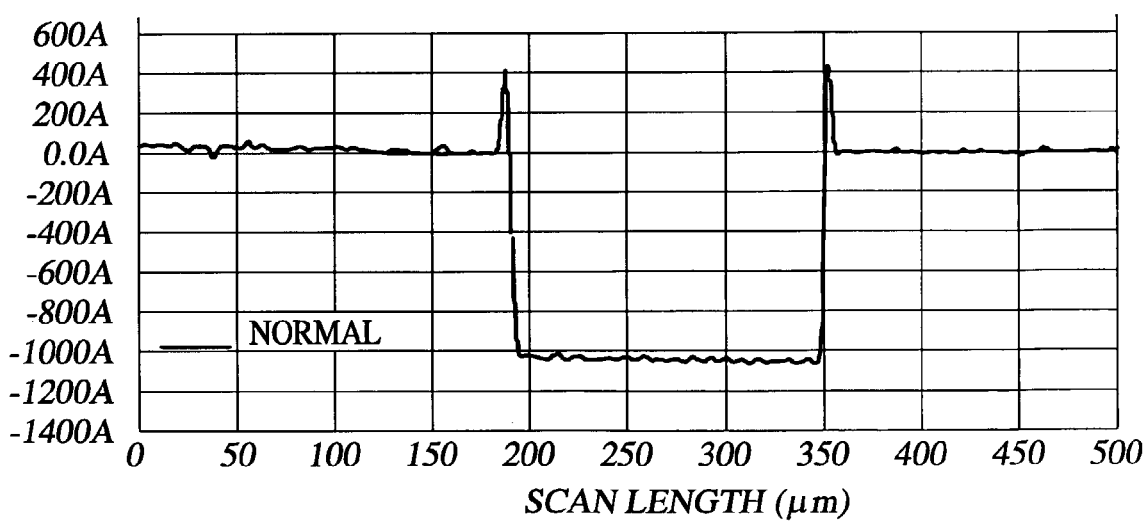
FIG. 11 is a profilometry scan of ten bilayers of Poly 1/SPS deposited on ten precursor bilayers of LPEI/SPS.
Figure 12:
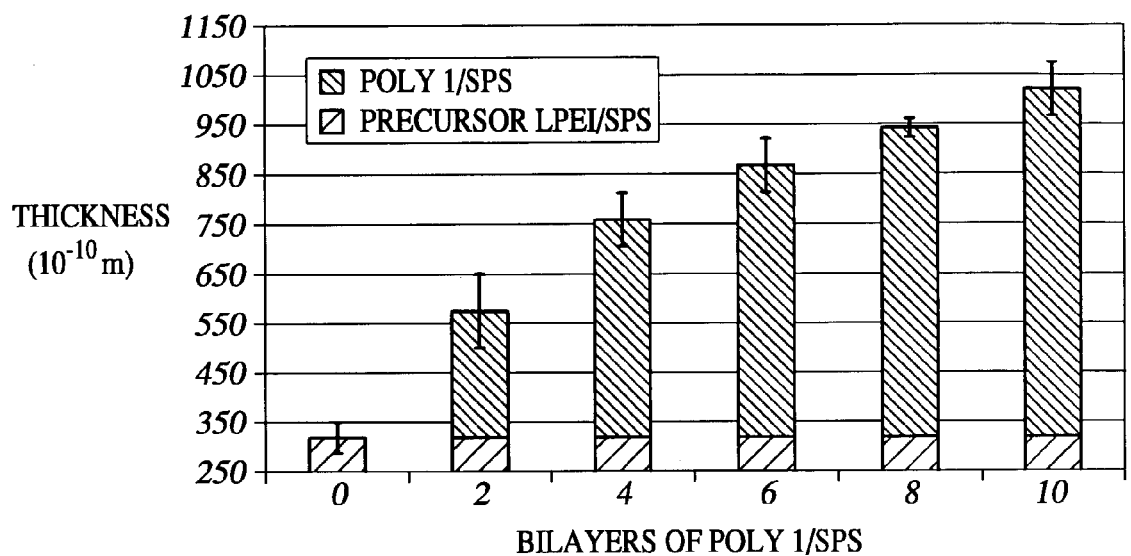
FIG. 12 illustrates the thickness change as bilayers of Poly 1/SPS are deposited on ten precursor bilayers of LPEI/SPS.

Growth of Poly1/SPS and Poly 1/PAA films: The deposition of multi-layer films was followed by ellipsometry as well as profilometry (see FIG. 11). Poly 1/SPS films composed of 10 bilayers (on top of the 10 substrate bilayers) were determined to be around 1000 Å thick by profilometry and around 1400 Å thick using ellipsometry. Bilayer growth proved to be directly proportional to film thickness (see FIG. 12). Films formed from 10 bilayers of Poly 1/PAA films were thicker than those formed from Poly 1/SPS (around 6000 Å). These results are consistent with previous studies showing a relationship between film thickness and pH for weak polyacid systems (Shiratori, S. S., et al., *Macromolecules*, 33:4213–4219, 2000). The films formed from both polymer systems were extremely smooth considering their thickness; the root mean square roughness (RMS) for both systems obtained by profilometry ranged from 16.9 Å to 60.2 Å.

Figure 13:
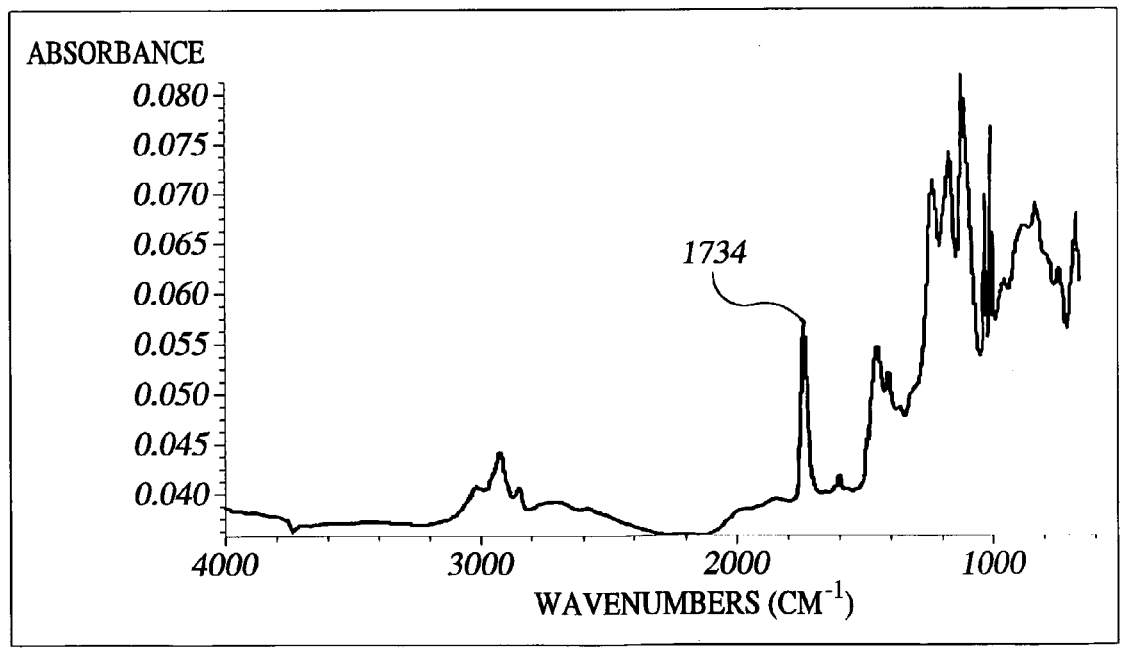
FIG. 13 is a reflective FTIR scan of ten bilayers of Poly 1/SPS deposited on ten precursor bilayers of LPEI/SPS on a gold substrate (1734 $cm^{-1}$ carboxyl stretch indicated)

To verify that Poly 1 was being incorporated in the films, Poly 1/SPS films were grown on gold substrates for analysis by reflective FTIR. The observation of a strong peak between 1725 and 1750 cm$^{-1}$ corresponding to the carboxyl stretch of Poly 1 confirms the presence of Poly 1 in the films (see FIG. 13). The Poly 1/SPS system was selected for the FTIR, rather than the Poly 1/PAA systems, to prevent the carboxyl group of the PAA from obscuring the CO stretch in Poly 1.

Figure 14:
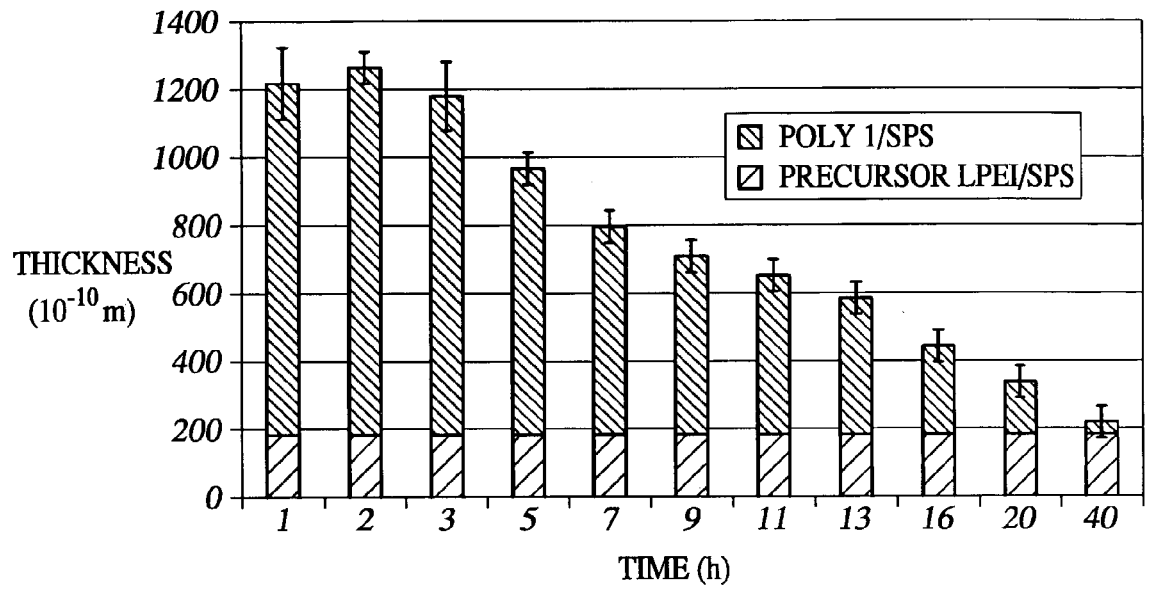
FIG. 14 illustrates the decomposition in PBS buffer at pH 7.4 (at 37° C.) of a thin film comprising Poly 1/SPS bilayers deposited on precursor bilayers of LPEI/SPS.
Figure 15:
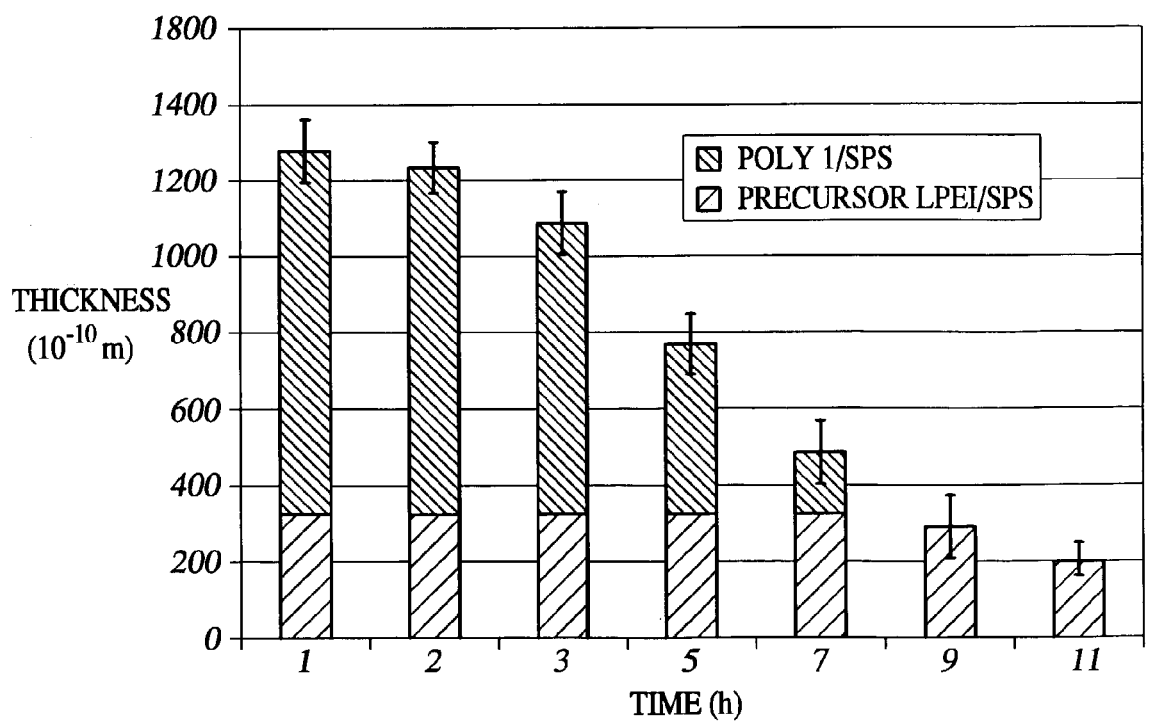
FIG. 15 illustrates the decomposition in TAE buffer at pH 8.3 (at 37° C.) of a thin film comprising Poly 1/SPS bilayers deposited on precursor bilayers of LPEI/SPS.

Decomposition of Poly 1/SPS and Poly 1/PAA films: Once procedures for the construction of films using Poly 1 were optimized, experiments to investigate film decomposition were performed. Films were incubated at pH 5.1, 7.4 and 8.3 in order to examine decomposition at pH and temperature values likely to be encountered in controlled release applications. Poly 1/SPS films decomposed over a 40-hour period in PBS pH 7.4 at 37° C. (see FIG. 14). Interestingly, decomposition appeared to occur by surface erosion and films remained smooth and consistent throughout the decomposition process, allowing decomposition to be monitored conveniently by ellipsometry. In general, the rate of decomposition increased with increasing pH. Poly 1/SPS films placed in TAE buffer at pH 8.3 decomposed in under nine hours (see FIG. 15) and more slowly under acidic conditions. These pH/rate data are consistent with a hydrolytic mechanism of degradation and erosion, similar to that previously observed for polymer 1 in solution (Lynn, D. M., 2000). Poly 1 is insoluble in aqueous media at pH 7.4, suggesting that degradation or erosion is occurring via hydrolysis rather than decomplexation and dissociation of layers of Poly 1 at higher pH.

Film erosion rates were also dependent on the structures of the incorporated polyanions. For example, while 100 nm thick Poly 1/SPS films eroded completely over a period of 40 hours at pH 7.4 (FIG. 2), 600 nm films formed from Poly 1 and PAA degraded completely over a period of 9 hours under identical conditions. This behavior is consistent with the pH/dissolution profile observed for other weak polyacid multilayer systems, in which the increased ionization of PAA at elevated pH contributes to repulsive electrostatic interactions (Sukhishvili, S. A., et al., *S. Macromolecules*, 35:301–310, 2002; Sukhishvili, S. A., et al., *J. Am. Chem. Soc.*, 122:9550–9551, 2000). Additionally, films containing thick layers of PAA often possess a lower overall effective crosslink density than more compact films constructed from strong polyelectrolytes such as SPS (Shiratori, S. S., 2000; Lvov, Y., et al., *Langmuir*, 9:481–486, 1993); the less crosslinked morphology may support more rapid permeation of water and breakdown of the polymer layers.

The ellipsometric data in FIG. 2 suggest that film erosion occurs gradually, rather than by the bulk deconstruction observed for weak polyacid or salt-deconstructed systems (Sukhishvili, S. A., 2002; Sukhishvili, S. A., 2000; For general examples of salt-induced "deconstruction" of polyelectrolyte multilayers, see: Dubas, S. T.; Schlenoff, J. B., *Macromolecules*, 34:3736–3740, 2001; Schüler, C., et al., *Biomacromolecules*, 2:921–926, 2001). Preliminary AFM analysis of partially eroded films is also consistent with this gradual erosion process—surface roughness values for partially eroded films (RMS roughness—6.9 nm) were less than the thickness of an average bilayer (10 nm) and surfaces were consistent over 1 μm (Hammond, P. T., 1998) portions of the film. We continue to investigate the factors governing erosion at various length scales and spatial resolutions, as the ability to control erosion in a "top-down" manner could introduce significant advantages from a release standpoint and allow precise control over the sequences by which one or more incorporated components are released. The different decomposition rates provide a potential means for controlling the exact decomposition rates of films by customization with these two or any other polyanions.

Figure 16:
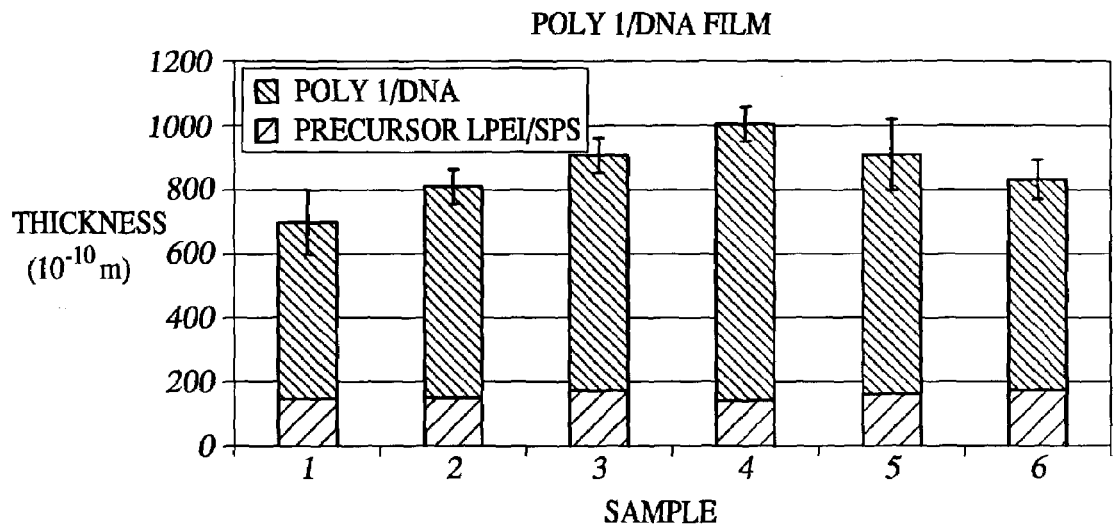
FIG. 16 illustrates the thickness of six different thin films comprising Poly 1/DNA bilayers deposited on ten precursor bilayers of LPEI/SPS.
Figure 17:
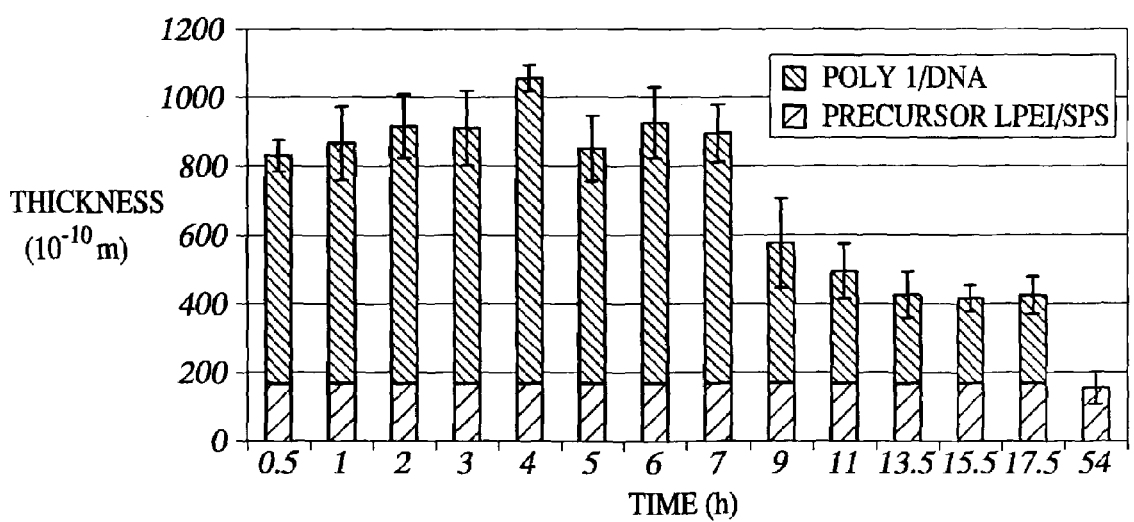
FIG. 17 illustrates the decomposition in PBS buffer at pH 7.4 (at 37° C.) of a thin film comprising Poly 1/DNA bilayers deposited on precursor bilayers of LPEI/SPS.

Controlled release of DNA from Poly 1/DNA films: Preliminary experiments designed to explore the application of these decomposable thin films to the controlled release of polyanions were done by adsorbing polyanionic dyes and calf thymus DNA into the decomposable polymeric films. Adsorption of DNA by electrostatic layer-by-layer deposition was achieved by the negative charge of the phosphate-sugar group that composes the helix. Poly 1/DNA films were deposited on silicon substrates previously prepared with ten precursor bilayers of LPEI/SPS. These films were measured by ellipsometry and film thickness ranged from 800 Å to 1000 Å (see FIG. 16). Poly 1/DNA films decomposed over a 50-hour period in PBS buffer pH 7.4 at 37° C. (see FIG. 17).

OTHER EMBODIMENTS

Those of ordinary skill in the art will appreciate that the foregoing has been a description of certain preferred embodiments of the present invention. This description is not intended to limit the spirit or scope of the present invention, as embodied in the following claims.

What is claimed is:

1. A decomposable film comprising a plurality of polyelectrolyte layers of alternating first and second charge, wherein decomposition of the film is characterized by sequential removal of at least a portion of the polyelectrolyte layers by alternating delamination of polyelectrolyte layers having the first charge and degradation of polyelectrolyte layers having the second charge.

2. The decomposable film of claim 1, wherein:
the film comprises alternating polycationic and polyanionic layers, and
decomposition of the film is characterized by hydrolytic degradation of a member of the polycationic layers, the polyanionic layers, and both.

3. The decomposable film of claim 1, wherein a portion of the polyelectrolyte layers comprises a member of a synthetic polyelectrolyte, a natural polyelectrolyte, and both.

4. The decomposable film of claim 1, wherein at least a portion of the polyelectrolyte layers comprises a polymer selected from polyesters, polyanhydrides, polyorthoesters, polyphosphazenes, polyphosphoesters, and any combination thereof.

5. The decomposable film of claim 4, wherein the polyesters are selected from poly(β-amino ester)s, poly(L-lactide-co-L-lysine), poly(serine ester), poly(4-hydroxy-L-proline ester), poly[α-(4-aminobutyl)-L-glycolic acid], and any combination thereof.

6. The decomposable film of claim 5, wherein the poly (β-amino ester) is

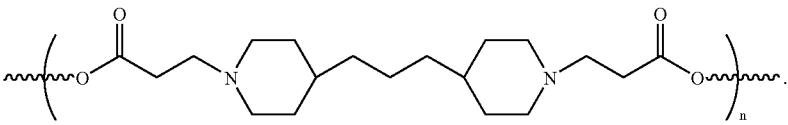

7. The decomposable film of claim 1, wherein the degradation is characterized by at least one of hydrolytic, thermal, enzymatic, and photolytic.

8. The decomposable film of claim 1, wherein the degradation rate of the layers varies such that the decomposition rate of the film is not a constant.

9. The decomposable film of claim 1, further comprising a layer of cells deposited on the surface of the film.

10. The decomposable film of claim 9, wherein the cells are selected from connective tissue cells, organ cells, muscle cells, nerve cells, stem cells, cancer cells, and any combination thereof.

11. The decomposable film of claim 1, wherein at least a portion of the layers comprise an entity selected from a biomolecule, a small molecule, a bioactive agent, and any combination thereof.

12. The decomposable film of claim 11, wherein a second portion of the layers comprise a second entity selected from a biomolecule, a small molecule, a bioactive agent, and any combination thereof.

13. The decomposable film of claim 11, wherein the concentration of the entity in the film varies with depth.

14. The decomposable film of claim 11, wherein the small molecule is a drug.

15. The decomposable film of claim 11, wherein the entity is associated with a polyelectrolyte in a layer of the film.

16. The decomposable film of claim 15, wherein the entity is associated via an interaction selected from covalent bond, a hydrogen bond, an electrostatic interaction, a van der Waals interaction, a hydrophobic interaction, a magnetic interaction and any combination of the above.

17. The decomposable film of claim 1, further comprising a member of a cell adhesion sequence, a targeting sequence, and both disposed in a top layer of the film.

18. The decomposable film of claim 1, wherein the film is deposited on a non-planar substrate.

19. The decomposable film of claim 18, wherein the film is deposited on a substrate having a shape selected from particles, tube, sphere, strand, coiled strand, and capillary network.

20. The decomposable film of claim 18, wherein degradation of the film enables dissolution of the substrate material.

21. The decomposable film of claim 18, wherein the substrate material diffuses through the film when the film-substrate combination is placed in a pre-selected medium.

22. The decomposable film of claim 18, wherein the substrate comprises a drug.

23. The decomposable film of claim 1, wherein the film is adapted and constructed as a hollow shell.

24. The decomposable film of claim 1, wherein the film is disposed on a substrate, wherein the surface properties of the substrate vary across a surface of the substrate.

25. The decomposable film of claim 1, wherein the film is disposed on a substrate comprising a material selected from metals, metal oxides, plastics, ceramics, silicon, glasses, mica, graphite, hydrogels, polymers, and any combination thereof.

26. The decomposable film of claim 25, wherein a primer layer is interposed between the film and the substrate, wherein the primer layer comprises a polyelectrolyte bilayer.

27. The decomposable film of claim 26, wherein the polyelectrolyte bilayer comprises a polymer selected from poly(styrene sulfonate) and poly(acrylic acid) and a polymer selected from linear poly(ethylene imine), poly(diallyl dimethyl ammonium chloride), and poly(allylamine hydrochloride).

* * * * *

UNITED STATES PATENT AND TRADEMARK OFFICE
CERTIFICATE OF CORRECTION

| | | |
|---|---|---|
| PATENT NO. | : 7,112,361 B2 | Page 1 of 1 |
| APPLICATION NO. | : 10/280268 | |
| DATED | : September 26, 2006 | |
| INVENTOR(S) | : David M. Lynn | |

It is certified that error appears in the above-identified patent and that said Letters Patent is hereby corrected as shown below:

Please delete the paragraph titled 'GOVERNMENT FUNDING' encompassing Column 1, lines 11-14:

"The work described herein was supported, in part, by grants from the National institutes of Health (GM26698; NRSA Fellowship #1 F32 GM20227-01). Accordingly, the Government may have certain rights in this invention."

and replace with:

--This invention was made with government support under Grant No. R01 EB000244 awarded by the National Institutes of Health. The government has certain rights in this invention.--

Signed and Sealed this
Sixteenth Day of October, 2012

David J. Kappos
*Director of the United States Patent and Trademark Office*